United States Patent [19]

Bolsman

[11] Patent Number: 4,873,025
[45] Date of Patent: Oct. 10, 1989

[54] ALKYLXYLENE SULFONATE COMPOSITIONS

[75] Inventor: Theodorus A. B. M. Bolsman, Amsterdam, Netherlands

[73] Assignee: Shell Oil Company, Houston, Tex.

[21] Appl. No.: 560,468

[22] Filed: Dec. 12, 1983

[30] Foreign Application Priority Data

Dec. 13, 1982 [GB] United Kingdom ............. 8235499

[51] Int. Cl.$^4$ ......................................... C07C 143/24
[52] U.S. Cl. .................................. 562/91; 252/8.554
[58] Field of Search ............... 260/505 R; 252/8.554

[56] References Cited

U.S. PATENT DOCUMENTS 2,467,131  4/1949  Hunt et al. .................... 260/505
3,933,201  1/1976  Kerfoot et al. ................ 166/275

FOREIGN PATENT DOCUMENTS 2116607  9/1983  United Kingdom .

OTHER PUBLICATIONS

P. H. Doe et al, J. Amer. Oil Chem. Soc., 55 (1978), 505–512.
P. H. Doe et al, J. Amer. Oil Chem. Soc., 55 (1978), 513–520.

*Primary Examiner*—Alan Siegel

[57] ABSTRACT

Compositions comprising alkylxylene sulfonate compounds of the formula

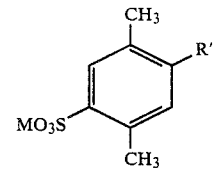

wherein R' represents a $C_6$ to $C_{20}$ alkyl group and wherein M represents a hydrogen, a metal, an ammonium or an amine ion, are useful as surfactants, particularly in enhanced oil recovery techniques.

2 Claims, No Drawings

ALKYLXYLENE SULFONATE COMPOSITIONS

BACKGROUND OF THE INVENTION

This invention relates to certain surfactant compositions comprising alkylxylene sulfonate compounds and to a method for displacing oil within a subterranean reservoir utilizing such compositions.

Compounds having valuable surface active properties are known to have been prepared from ortho-xylene by alkylation and then sulfonation. A mixture of several different isomers results, the predominant one of which is usually of the structure

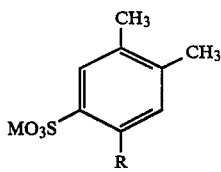

wherein R is an alkyl group, typically of about 6 to 20 carbon atoms, and M represent a hydrogen, a metal, an ammonium or an amine ion.

The alkyl ortho-xylene sulfonates have been recommended for use in various detergent compositions. In addition, because of their chemical and thermal stability, they are recognized as useful in various enhanced oil recovery techniques. Their application in oil recovery services is restricted to relatively low-salinity reservoirs, however, because the alkyl ortho-xylene sulfonates suffer from a limited solubility and salt-tolerance in water.

It is the principal object of the present invention to provide a novel surfactant composition characterized by favorable surfactant properties and stability, but one which is more soluble under high-salinity conditions.

SUMMARY OF THE INVENTION

The present invention relates to compositions comprising alkylxylene sulfonate compound(s), in which a substantial portion of the alkylxylene sulfonate fraction is made up of one or more compounds of the formula

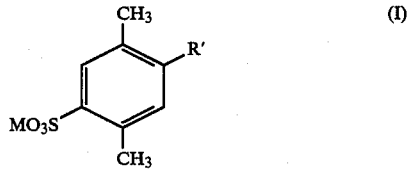

wherein R' represents a $C_6$ to $C_{20}$ alkyl group and M represents a hydrogen, a metal, an ammonium, or an amine ion.

Such compositions are derived from para-xylene, or from xylene isomer mixtures comprised in substantial part of para-xylene, by alkylation with $C_6$ to $C_{20}$ alkyl groups followed by sulfonation.

The compositions of the invention are characterized by enhanced solubility in water, particularly brines, relative to conventional alkylxylene sulfonate products.

DESCRIPTION OF THE PREFERRED EMBODIMENTS

The beneficial solubilization properties of the surfactant compositions according to the invention are believed to relate to a molecular structure in which the long chain, $C_6$ to $C_{20}$ alkyl substituent is positioned directly opposite to the sulfonate moiety. The alkyl substituent points away from the direction of the dipole moment, a fact which positively influences water solubility as well as the packing of molecules at an oil/water interface. It has been determined that compounds of formula I are not present in any significant quantity or the mixture of isomers which results from conventional alkylation and sulfonation of ortho-xylene, and that in such a mixture no more than about 30% of the several isomers which are produced are characterized by an alkyl substituent directly opposite from the sulfonate moiety. Alkylation and sulfonation of meta-xylene in a conventional manner typically results in very large part (e.g., 90% or more) in an alkylxylene sulfonate in which the sulfonate group is not directly opposite from, but is instead in a meta position relative to, the $C_6$ to $C_{20}$ alkyl group.

Compositions of the invention suitably include other alkylxylene sulfonate isomers, in addition to those of formula I. This is particularly true when the composition is derived from a para-xylene starting material which is less than completely pure and also contains ortho- and/or meta-xylenes. However, blends of the various product isomers are very useful and are considered part of the invention so long as the alkylxylene sulfonate fraction as a whole contains a substantial amount of (e.g., about 25% or more) of the isomer described by formula I. The properties of such blends benefit from increasing proportions of the product as is derived from para-xylene. Accordingly, a composition which contains the formula I isomer in a quantity that is at least about 50% of the alkylxylene sulfonate fraction is preferred, while a quantity of at least 75% is more preferred. Most preferred are compositions in which the alkylxylene sulfonate fraction consists essentially of isomers of formula I, or, in other words wherein at least about 95% of the isomers are of the formula I structure.

The carbon chain length of the alkyl substituent has an important influence upon many of the properties of the alkylxylene sulfonate, particularly upon those properties relating to solubility in brine and oil mixtures. Alkyl groups having 6 to 20 carbon atoms are generally considered suitable for such surfactants having desirable solubility properties, while alkyl groups having 8 to 18 carbon atoms are preferred. Particularly preferred are alkylxylene sulfonates in which a large proportion of the alkyl groups are in the $C_8$ to $C_{14}$ range. Mixtures of different alkyl groups are in many cases preferred. A specific example of a preferred mixture of alkylxylene sulfonate molecules of formula I is one in which the alkyl groups are about 35%w $C_8$ to $C_{10}$, 40%w $C_{11}$ and $C_{12}$ and 25%w $C_{13}$ and $C_{14}$.

The $C_6$ to $C_{20}$ alkyl group of the molecule may be linear or branched and primary or secondary. Linear alkyl groups and/or secondary alkyl groups are preferred, and alkyl groups that are both linear and secondary are particularly preferred. Most preferably, a linear, secondary alkyl group has the general structure $CH_3$—$CH$—$R^4$, wherein $R^4$ represents a $C_4$ to $C_{18}$ n-alkyl group. Alkylxylene sulfonates having alkyl groups of this structure may be produced by alkylating the aromatic nucleus with linear alpha-olefins.

Compositions according to the invention are conveniently prepared by alkylating a para-xylene reactant (or a reactant mixture of xylene isomers containing at least about 25%w para-xylene), sulfonating the resulting alkylate, and, optionally, converting the product alkylxylene sulfonic acid(s) into the salts. The alkylation may be carried out in a manner known for analogous compounds, e.g., by a Friedel-Crafts reaction using a alkyl halide, alkanol, or alkene reactant, in the presence of a Lewis acid catalyst. Preferably, the catalyst is hydrogen fluoride or an activated clay, for example, a clay marketed under the tradename Fulcat. The purity of the alkylxylene intermediate can be improved by topping and tailing distillations to obtain products containing more than about 95% of the desired mono-alkyl substituted xylenes.

Sulfonation of the alkylxylenes can then be performed in a manner known for analogous compounds, e.g., by contacting with concentrated sulfuric acid and/or sulfur trioxide. The structure of the sulfonic acids (and corresponding salts) which result is not greatly dependent on sulfonation reaction conditions.

Preferably, the sulfonic acid is neutralized with a base to give a product of formula I for which M represents any of the ionsconventionally present in sulfonate salts, i.e., a metal ion such as Na, K, Ca, Mg, or Fe, an ammonium ion, or an amine ion such as one of the formula HNPQR, wherein P, Q, and R represent organic groups, for example, triethanolamine. Most preferably M represents a sodium ion.

Compositions according to the invention may take the specific form of formulations useful for enhanced oil recovery applications. In this regard, the invention particularly relates to compositions typically prepared for such service, comprising, for instance, about 2.0 to 10% by volume (%v) of the alkylxylene sulfonates, 0.5 to 2.0%v of a $C_2$ to $C_6$ aliphatic alcohol, 0.05 to 2.0%v of another surfactant, e.g., an alcohol ethoxylate, an alcohol ethoxysulfate, or an alcohol ethoxysulfonate, and 0 to 2.0%v of a (carrier) oil, the balance being water.

The invention also relates to a method for displacing oil within a subterranean reservoir, which comprises injecting a composition in accorance with the invention and then injecting water, optionally water containing a polymeric thickener. In such applications, compositions of the invention have a tendency to form stable microemulsions with the oil and with brine which may be present. Such microemulsions have advantage over ordinary solutions because they are characterized by low interfacial tensions and also because in this form the surfactants have less of a tendency to be retained by formation rock of the reservoir. As has been indicated, the compositions of the invention have an enhanced tolerance for salt in such oil recovery processes.

The invention is further illustrated by the following examples.

EXAMPLE 1

Preparation of sodium alkylxylene sulfonates

A. Alkylation. Linear alpha-olefins of varying chain lengths (in the $C_8$ to $C_{14}$ range) were reacted with substantially pure ortho-xylene, meta-xylene, or para-xylene in a stirred batch reactor provided with a condenser, at atmospheric pressure and at a temperature of 138° to 145° C. The xylene to olefin molar ratio was in the range of 5 to 10. An activated clay, which is commercially available under the trade-mark Fulcat 22B was used as catalyst. The progress of the reaction was, in each case, followed by periodic GLC-analyses. When analysis showed that all the olefin had reacted, typically after about five hours, the catalyst was filtered off, and the remaining unreacted xylene was then flashed off in a rotating evaporator apparatus. Products containing 93-99% of the mono-alkyl substituted xylenes were obtained via topping and tailing distillations.

B. Sulfonation. Each of the alkylated xylene products of step A was then sulfonated with gaseous sulfur trioxide in a stirred batch reactor at a temperature of 50° C. The sulfur trioxide reactant was introduced in a dilute (7% by volume mixture in nitrogen and in a total quantity slightly in excess of that required for sulfonation (1.05 moles sulfur trioxide per mole of alkylated xylene). The $SO_3$ was added over a period of 2.5 hours, after which the reaction was allowed to continue for yet another half hour at 50° C. and then to age for one further day at ambient temperature. The sulfonated products were each neutralized with a 46%w aqueous NaOH solution. During neutralization the para-xylene derived materials generated viscous pastes, so that additional water was added to lower the viscosity. Product materials were off-white foams with concentrations of approximately 1.6 meq/g active matter, as determined by two-phase titration. Only the para-xylene derived product was in accordance with the invention, and the alkylxylene sulfonate fraction of that product consisted essentially of isomers illustrated by formula I.

EXAMPLE 2

The comparative properties of alkylxylene sulfonate products derived from para-xylene, ortho-xylene, and meta-xylene were determined in surfactant-brine-crude oil mixtures. In each case, the surfactant was a sodium alkylxylene sulfonate having a linear alkyl group, and was present in a concentration of 1 meq/18 of ml of the total mixture. Secondary butanol was in each case added as co-surfactant in a quantity (unless otherwise indicated) which equaled 0.6%w of the total mixture. The influence of alkyl groups of different carbon numbers was also tested. The brine, simulating water from a crude oil reservoir, was a solution containing NaCl and $CaCl_2$ in a molar ratio of 231.

The following Table indicates several parameters of the different surfactants which are important to their application in oil recovery systems. (In the Table "o" represents alkylxylene sulfonates derived form ortho-xylene, "m" represents those derived from meta-xylene, and "p" represents those derived from para-xylene.) One tabulated parameter is the midpoint salinity (MPS) of the mixture, which directly reflects the water solubility of the surfactant. Midpoint salinity is defined as that concentration of salt in a brine (expressed in % SRW, where 10.0 g/l NaCl and 0.0821 g/l $CaCl_2$ correspond to 100% SRW) that causes the surfactant-brine-oil system to form a middle microemulsion phase containing equal amounts of oil and brine.

Another tabulated parameter is the salinity window, which is defined as the range of brine concentration in the surfactant-brine-oil system over which the microemulsin is maintained in the desired type III phase behavior. Both the midpoint salinity and the salinity windows are important to the performance of the surfactant in micellar flooding methods for oil recovery. The salinity window (SW) is also expressed in % SRW.

The solubilization parameter (SP) is defined as the volume of oil per unit volume of surfactant in the microemulsion phase at midpoint salinity. The higher the SP the more efficient the surfactant is in solubilizing oil.

Higher SP values correspond to lower interfacial tension between oil-microemulsion and microemulsion-brine phases at MPS.

MPS, SW, and SP values were determined by increasing the concentration of salt in the brine phase, keeping other experimental conditions constant. All measurements were made at 67° C.

TABLE

| alkylxylene sulfonate | alkyl group weight fraction | | | MPS | SW | |
|---|---|---|---|---|---|---|
| (o, m or p) | $C_8$–$C_{10}$ | $C_{11}$–$C_{12}$ | $C_{13}$–$C_{14}$ | % SRW | % SRW | SP |
| o* | 35 | 40 | 25 | 139 | 50 | 5.6 |
| o* | 100 | 0 | 0 | 370 | 275 | 3.0 |
| m*[(1)] | 35 | 40 | 25 | 413 | 180 | 7.2 |
| p | 35 | 40 | 25 | 670 | 170 | 9.2 |
| p | 20 | 30 | 50 | 740 | 100 | 10.2 |
| p | 10 | 20 | 70 | 500 | 55 | 12.0 |
| p | 0 | 100 | 0 | 645 | 100 | 11.8 |
| p | 0 | 0 | 100 | 350 | 70 | 11.0 |
| 3 parts o and 1 part p[(2)] | 35 | 40 | 25 | 231 | 80 | 6.8 |
| 1 part o and 1 part p[(2)] | 35 | 40 | 25 | 365 | 120 | 7.4 |
| 1 part o and 3 parts p[(2)] | 35 | 40 | 25 | 531 | 175 | 9.0 |

*Comparative
[(1)]containing only 0.33% w of s-butanol
[(2)]containing only 0.28% w of s-butanol The tabulated data indicates that the para-xylene derived surfactant has a water solubility meaningfully higher than that of either of the corresponding ortho-xylene or meta-xylene derived products. In particular the para-xylene products are shown to reach MPS at considerably higher salinities. The solubilization parameter (SP) is similarly greater for the para-xylene derived products. Mixtures are also shown to directly benefit from the presence of the $C_6$ to $C_{20}$ alkyl substituted para-xylene sulfonates.

What is claimed is:

1. A surface active composition consisting essentially of alkylxylene sulfonate compounds of the formula

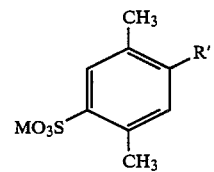

wherein M represents a hydrogen, a metal, an ammonium or an amine ion and R' represents a $C_8$ to $C_{10}$ alkyl group in about 35 percent by weight of the compounds, R' represents a $C_{11}$ or $C_{12}$ alkyl group in about 40 percent by weight of the compounds, and R' represents a $C_{13}$ or $C_{14}$ alkyl group in about 25 percent by weight of the compounds.

2. The composition according to claim 1, wherein M represents a sodium ion.